US00PP14825P2

(12) United States Plant Patent
Heims

(10) Patent No.: US PP14,825 P2
(45) Date of Patent: May 25, 2004

(54) ×HEUCHERELLA PLANT NAMED 'SUNSPOT'

(50) Latin Name: ×*Heucherella sp.*
Varietal Denomination: Sunspot

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 58 days.

(21) Appl. No.: 10/452,951

(22) Filed: Jun. 2, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Klarquist Sparkman, LLP

(57) ABSTRACT

A new and distinct cultivar of ×Heucherella plant characterized by its distinctive golden to lime green foliage with a maroon blotch.

1 Drawing Sheet

Botanical classification: ×Heucherella sp.
Cultivar denomination: 'Sunspot'.

BACKGROUND OF THE INVENTION

The present invention relates to a new and distinct intergeneric hybrid between Heuchera and Tiarella, or ×Heucherella, and given the cultivar name 'Sunspot'. Both genera, Heuchera and Tiarella, are of the family Saxifragaceae.

This new cultivar originated from a mutation in tissue culture from ×Heucherella 'Dayglow Pink' (U.S. Plant Pat. No. 12,164).

SUMMARY OF THE INVENTION

This new Heucherella is unique in its golden to lime green foliage unique in the ×Heucherella with a maroon starry blotch in the middle and characterized by:

1. Small, lobed leaves.
2. Intense pink flowers on maroon peduncles.
3. Tight habit.
4. Excellent vigor.

The new variety has been reproduced only by asexual propagation (division and tissue culture). Each of the progeny exhibits identical characteristics to the original plant. Asexual propagation by division and tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows the two year old plant growing in a two-gallon pot in Canby, Oreg.

DETAILED PLANT DESCRIPTION

The following is a detailed description of the new ×Heucherella hybrid based on observations of two-year-old specimens grown in a one-gallon pot in the greenhouse in Canby, Oreg. The color descriptions are all based on The Royal Horticultural Society Colour Chart.

Botanical name: ×Heucherella sp.
Cultivar name: 'Sunspot'.
Plant:
- *Type.*—Herbaceous perennial.
- *Form.*—Basal rosette.
- *Hardiness.*—USDA Zone 5.
- *Size.*—18 cm tall and 35 cm wide.

Leaf:
- *Type.*—Simple.
- *Arrangement.*—Rosette.
- *Shape.*—Broadly ovate.
- *Lobing/division.*—3 main lobes with each of these shallowly lobed.
- *Venation.*—Palmate.
- *Margins.*—Crenate.
- *Apex.*—Obtuse and often cupped.
- *Base.*—Cordate and overlapping.
- *Blade size.*—Ranges from 6.5 to 9.5 cm long and 6 to 9.5 cm wide.
- *Aspect.*—Matte.
- *Texture.*—Puberulous.
- *Petiole length.*—Ranges from 10 to 15 cm.
- *Petiole texture.*—Hispid and with glandular hairs.
- *Petiole color.*—Greyed Purple 187D.
- *Leaf color.*—Leaves open in spring a golden color and become greener with age. New spring leaves — Between Yellow Green 145A with slightly more gold and Yellow Green 151A with slightly more green. Reddish pattern in the center, Greyed Purple 185A. Spring leaves — upper surface — Yellow Green 145A, with the pattern Greyed Purple 185C. Lower surface — Closest to Yellow Green 145B. Winter leaves — Yellow Green 146B with reddish veins, Greyed Purple 183A.

Inflorescence:
- *Type.*—Thyrse.
- *Number of flowers.*—Ranges from 40 to 50 per thyrse, on top 8 cm of peduncle.

*Peduncle.*—With 1 to 2 leaves and branches. Height — 40 cm. Diameter — 0.2 cm. Color — Burgundy, Greyed Purple 184A. Vestiture — Pubescent.

*Pedicel.*—Length — to 0.7 cm Vestiture — Pubescent. Color — Greyed Purple 184A

*Bloom period.*—Early April to late May. Sporadic rebloom until fall in Canby, Oreg.

Flower bud:

*Size.*—0.45 cm deep and 0.25 cm wide.

*Description.*—Oblong, downfacing, pubescent.

*Color.*—Deep pink, Red Purple 67C.

Flower:

*Type.*—Perfect, sepals petaloid.

*Shape.*—Rotate or stellate.

*Size.*—0.8 cm wide and 0.5 cm deep.

*Petal count.*—5.

*Petal shape.*—Obovate with a clawed base.

*Petal size.*—0.4 cm long and 0.1 cm wide.

*Petal color.*—Light pink, Red Purple 62D.

*Petal texture.*—Satiny.

*Calyx.*—Petaloid, divided ¾ way to the base, with hairs.

*Calyx shape.*—Campanulate with 5 rounded lobes, revolute.

*Calyx size.*—0.8 cm wide and 0.5 cm deep.

*Calyx texture.*—Glandular pubescent.

*Calyx color.*—Outside: Red Purple 68B. Inside: Red Purple 68D.

*Stamen number.*—5, sterile.

*Pistil.*—White 55D.

*Fragrance.*—None.

*Lastingness.*—A thyrse blooms for about 2 weeks on the plant.

Fruit and seed: None. The plant does not form fruit or seed.

*Fertility.*—Sterile.

Disease tolerance: Excellent disease resistance.

COMPARISONS TO SIMILAR ×HEUCHERELLA

Compared to Heucherella 'Dayglow Pink' (U.S. Plant Pat. No. 12,164), this new cultivar has golden to lime green foliage rather than green with a maroon blotch rather than brown.

I claim:

1. A new and distinct cultivar of ×Heucherella plant substantially as shown and described, characterized by its distinctive golden to lime green foliage with a maroon blotch.

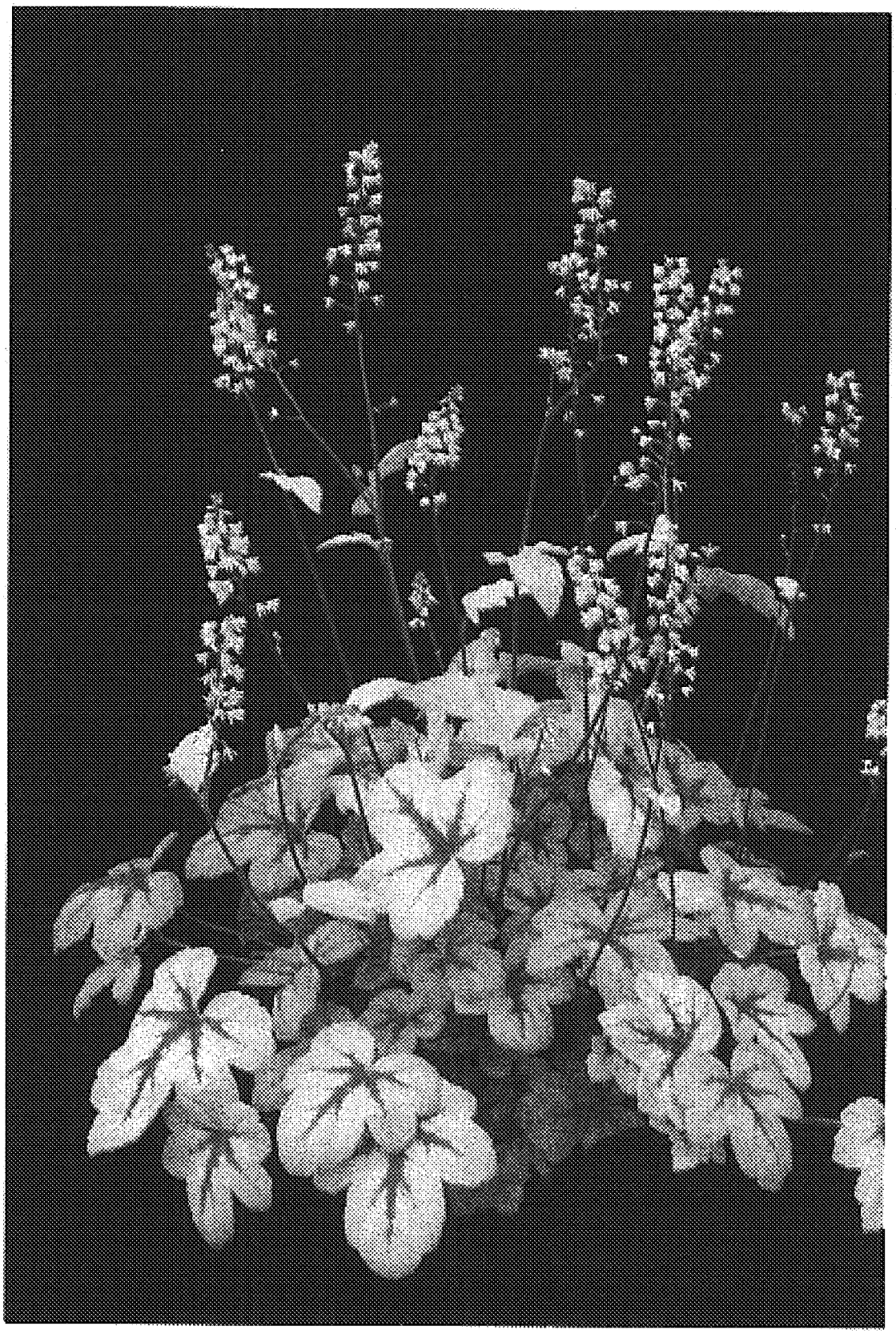

* * * * *